(12) United States Patent
Hu et al.

(10) Patent No.: US 10,189,948 B2
(45) Date of Patent: Jan. 29, 2019

(54) ISATIN COPOLYMERS HAVING INTRINSIC MICROPOROSITY

(71) Applicant: DOW GLOBAL TECHNOLOGIES LLC, Midland, MI (US)

(72) Inventors: Xiaolian Hu, Shanghai (CN); Zhe Du, Shanghai (CN); Robert E. Hefner, Jr., Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/563,976

(22) PCT Filed: Jun. 24, 2015

(86) PCT No.: PCT/CN2015/082173
§ 371 (c)(1),
(2) Date: Oct. 3, 2017

(87) PCT Pub. No.: WO2016/206008
PCT Pub. Date: Dec. 29, 2016

(65) Prior Publication Data
US 2018/0142065 A1    May 24, 2018

(51) Int. Cl.
| | |
|---|---|
| *C08G 8/02* | (2006.01) |
| *C08J 5/22* | (2006.01) |
| *B01D 67/00* | (2006.01) |
| *B01D 71/62* | (2006.01) |
| *B01D 71/76* | (2006.01) |
| *C08G 16/00* | (2006.01) |
| *C08G 61/12* | (2006.01) |
| *C08G 73/06* | (2006.01) |
| *B01D 71/38* | (2006.01) |
| *B01D 69/02* | (2006.01) |
| *B01D 71/44* | (2006.01) |
| *C07D 209/38* | (2006.01) |
| *B01D 71/56* | (2006.01) |

(52) U.S. Cl.
CPC ......... *C08G 73/0672* (2013.01); *B01D 69/02* (2013.01); *B01D 71/38* (2013.01); *B01D 71/44* (2013.01); *B01D 71/76* (2013.01); *C08G 8/02* (2013.01); *B01D 71/56* (2013.01); *B01D 2325/02* (2013.01); *C07D 209/38* (2013.01)

(58) Field of Classification Search
CPC ........ C08G 61/124; C08G 8/02; C08G 16/00; C08G 61/12; C08G 73/0672; C08G 2261/124; C08G 2261/1412; C08G 2261/1422; C08G 2261/1426; C08G 2261/1428; C08G 2261/516; B01D 67/0006; B01D 71/62; B01D 71/76; C08J 5/2256
See application file for complete search history.

(56) References Cited

U.S. PATENT DOCUMENTS

| | | |
|---|---|---|
| 5,629,084 A | 5/1997 | Moya |
| 7,410,525 B1 | 8/2008 | Liu et al. |
| 7,485,173 B1 | 2/2009 | Liu et al. |
| 7,690,514 B2 | 4/2010 | McKeown et al. |
| 7,758,751 B1 | 7/2010 | Liu et al. |
| 7,771,857 B2 | 8/2010 | Fritsch et al. |

(Continued)

FOREIGN PATENT DOCUMENTS

| | | |
|---|---|---|
| KR | 20150027605 | 3/2015 |
| WO | 2005113121 | 12/2005 |

(Continued)

OTHER PUBLICATIONS

Grogojo et al., Adv. Funct. Mater. 2014, 24, 4729-4737.

(Continued)

*Primary Examiner* — Shane Fang
(74) *Attorney, Agent, or Firm* — Kenneth Crimaldi

(57) ABSTRACT

A copolymer including a repeating unit represented by (I) wherein: Y is selected from: a carboxylic acid, sulfonic, phosphorous acid and phosphoric acid and their corresponding salt or ester; imino, amide, nitrile, hydrogen, hydroxyl and alkyl comprising from 1 to 6 carbon atoms; and $R_1$, $R_2$, $R_3$, and $R_4$ are independently selected from: hydrogen, alkyl groups comprising from 1 to 6 carbon atoms, and $R_1$ and $R_2$ may collectively form a ketone group or a 9, 9'-fluorene group, and $R_3$ and $R_4$ may collectively form a ketone group or a 9, 9'-fluorene group; $R_5$ and $R_6$ are independently selected from: a bond and an alkylene group comprising from 1 to 6 carbon atoms; $R_7$ is selected from: hydrogen, alkyl, aryl, aralkyl and heteroaryl groups comprising from 1 to 8 carbon atoms which may be unsubstituted or substituted with carboxylic acid, sulfonic acid and phosphoric acid and their corresponding salt or ester, imino and amide; and X and X' are independently selected from: a carboxylic acid, sulfonic acid and phosphoric acid and their corresponding salt or ester, imino and amide; nitrile, hydrogen, alkyl having from 1 to 6 carbon atoms and alkoxy having from 1 to 6 carbon atoms.

8 Claims, No Drawings

(56) References Cited

U.S. PATENT DOCUMENTS

| | | |
|---|---|---|
| 7,806,962 B2 | 10/2010 | Liu et al. |
| 7,943,543 B1 | 5/2011 | Liu et al. |
| 8,048,198 B2 | 11/2011 | Liu et al. |
| 8,056,732 B2 | 11/2011 | McKeown et al. |
| 8,132,677 B2 | 3/2012 | Liu et al. |
| 8,575,414 B2 | 11/2013 | Liu et al. |
| 8,613,362 B2 | 12/2013 | Liu et al. |
| 8,623,928 B2 | 1/2014 | Du et al. |
| 8,686,104 B2 | 4/2014 | Du et al. |
| 8,809,488 B2 | 8/2014 | Du et al. |
| 8,814,982 B2 | 8/2014 | Liu et al. |
| 8,894,859 B2 | 11/2014 | Livingston et al. |
| 8,969,628 B2 | 3/2015 | Priske et al. |
| 9,018,270 B2 | 4/2015 | McKeown et al. |
| 9,126,185 B2 | 9/2015 | Laskoski |
| 9,238,202 B2 | 1/2016 | Liskey et al. |
| 2004/0198587 A1 | 10/2004 | McKeown et al. |
| 2006/0246273 A1 | 11/2006 | McKeown et al. |
| 2007/0209505 A1 | 9/2007 | Liu et al. |
| 2009/0031897 A1 | 2/2009 | Liu et al. |
| 2009/0120875 A1 | 5/2009 | Liu et al. |
| 2009/0155464 A1 | 6/2009 | Liu et al. |
| 2010/0130634 A1 | 5/2010 | Fritsch |
| 2012/0157743 A1 | 6/2012 | Liu et al. |
| 2012/0273421 A1 | 11/2012 | Perry et al. |
| 2013/0085191 A1 | 4/2013 | Laskoski |
| 2013/0112619 A1 | 5/2013 | Livingston et al. |
| 2013/0146538 A1 | 6/2013 | Liu et al. |
| 2013/0172433 A1 | 7/2013 | McKeown et al. |
| 2013/0217799 A1 | 8/2013 | Visser et al. |
| 2013/0220415 A1* | 8/2013 | Zhou .................. H01L 31/0256 136/256 |
| 2013/0247756 A1 | 9/2013 | Li et al. |
| 2013/0267616 A1 | 10/2013 | McKeown et al. |
| 2014/0251897 A1 | 9/2014 | Livingston et al. |
| 2014/0255636 A1 | 9/2014 | Odeh et al. |
| 2015/0148439 A1 | 5/2015 | Eddaoudi et al. |
| 2015/0165383 A1 | 6/2015 | Liskey et al. |
| 2015/0239806 A1 | 8/2015 | Wendland |

FOREIGN PATENT DOCUMENTS

| | | |
|---|---|---|
| WO | 2012035328 | 3/2012 |
| WO | 2014186108 | 11/2014 |
| WO | 2015018576 | 2/2015 |
| WO | 2015095026 | 6/2015 |
| WO | 2015095034 | 6/2015 |
| WO | 2015095044 | 6/2015 |
| WO | 2015129925 | 9/2015 |
| WO | 2016148869 | 9/2016 |
| WO | 2016161367 | 10/2016 |
| WO | 2016195977 | 12/2016 |
| WO | 2017030450 | 2/2017 |
| WO | 2017091357 | 6/2017 |

OTHER PUBLICATIONS

Fritsch et al., Journal of Membrane Science 401-402 (2012) 222-231.

Xiaohua Ma et al., Synthesis and Gas Transport Properties of Hydroxyl-Functionalized Polyimides with Intrinsic Microporosity, Macromolecules, vol. 45, No. 9 (May 8, 2012).

Xiaohula Ma et al., Novel Spirobifluorene and Dibromospirobifluorene-based Polyimides of Intrinsic Microporosity for Gas Separation Applications, Macromolecules, vol. 46, No. 24, (Dec. 23, 2013).

Fu Yun Li et al., High-Performance Thermally Self-Cross-Linked Polymer of Intrinsic Microporosity (PIM-1) Membranes for Energy Development, Macromolecules, vol. 45, No. 3, (Feb. 14, 2012).

* cited by examiner

ISATIN COPOLYMERS HAVING INTRINSIC MICROPOROSITY

FIELD

The invention relates to microporous copolymers derived from monomers including isatin and spirobisindane moieties. The copolymers have particular utility as membranes useful in gas and liquid separations.

INTRODUCTION

Polymers with intrinsic microporosity (PIMS) are characterized by having macromolecular structures that are both rigid and contorted so as to have extremely large fractional free volumes. Examples include poly(1-trimethylsilyl-1-propyne) (PTMSP), poly(4-methyl-2-pentyne) (PMP) and polybenzodioxane (PIM-1). Because of their exceptional free volume, all are extremely permeable. See: Baker, Membrane Technology and Applications, $3^{rd}$ ed., (2012), and Polymers of Intrinsic Microporosity, Enc. Polymer Sci. & Tech., (2009)—both by John Wiley & Sons Ltd. See also: WO2005/113121; US2004/01985587; US2013/0146538; US2013/0172433; US2013/0267616; US2014/0251897; U.S. Pat. No. 9,018,270; U.S. Pat. No. 8,623,928; U.S. Pat. No. 8,575,414; U.S. Pat. No. 8,056,732; U.S. Pat. No. 7,943,543; U.S. Pat. No. 7,690,514 and U.S. Pat. No. 7,410,525 which are incorporated herein in their entirety. By way of example, US2014/0251897 describes a thin layer composite membrane including a thin selective layer of a networked microporous polymer having intrinsic microporosity formed via an interfacial polymerization of monomers having concavity (e.g. spirobisindanes, bisnapththalenes, ethanoanthracenes). U.S. Pat. No. 7,771,857 describes polymer electrolyte membranes polymerized from monomer units including aromatic polyarylenes groups with proton-conducting functional groups.

SUMMARY

The invention includes copolymers having intrinsic microporosity and membranes made therefrom. In one embodiment, the invention includes a copolymer including a repeating unit represented by Formula I.

Formula I:

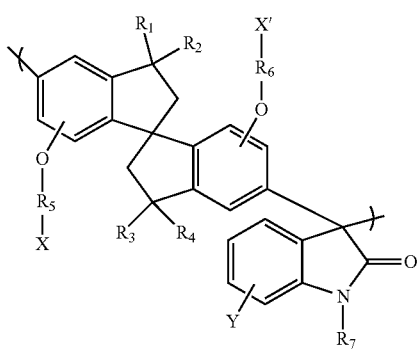

wherein:

Y is selected from: a carboxylic acid, sulfonic, phosphorous acid and phosphoric acid and their corresponding salt or ester, imino, amide; nitrile, hydrogen, hydroxyl and alkyl comprising from 1 to 6 carbon atoms; and $R_1$, $R_2$, $R_3$, and $R_4$ are independently selected from: hydrogen, alkyl groups comprising from 1 to 6 carbon atoms, and $R_1$ and $R_2$ may collectively form a ketone group or a 9,9'-fluorene group, and $R_3$ and $R_4$ may collectively form a ketone group or a 9,9'-fluorene group;

$R_5$ and $R_6$ are independently selected from: a bond and an alkylene group comprising from 1 to 6 carbon atoms;

$R_7$ is selected from: hydrogen, alkyl, aryl, aralkyl and heteroaryl groups comprising from 1 to 8 carbon atoms which may be unsubstituted or substituted with carboxylic acid, sulfonic acid and phosphoric acid and their corresponding salt or ester, imino and amide; and X and X' are independently selected from: a carboxylic acid, sulfonic acid and phosphoric acid and their corresponding salt or ester, imino and amide; nitrile, hydrogen, alkyl having from 1 to 6 carbon atoms and alkoxy having from 1 to 6 carbon atoms.

In additional embodiments, the invention includes thin films, coatings and membrane made using the subject copolymers, including B-stage and network forms of the copolymers useful in the formation of such films, coatings and membranes.

DETAILED DESCRIPTION

In a preferred embodiment, the subject copolymers (also referred to herein as "polymers") are polymers having intrisic microporosity. The term "intrinsic microporosity" refers to a polymer having a continuous network of interconnected intermolecular voids which form a direct consequence of the shape and rigidity of at least a portion of the components monomers of the polymer. The term "microporous" refers to a material having an interconnected system of voids of a diameter less than 2 nm as defined by the IUPAC. Preferably, the subject copolymers have average pore diameters of from 0.2 to 20 nm as determined by standard bubble point test (e.g. ASTM F316-03 (2011)). The copolymers also have high apparent surface areas (e.g. greater than 100 $m^2/g$, and more preferably greater than 150 $m^2/g$ as determined by the Brunauer-Emmett-Teller (BET) method.

In several embodiments, the subject copolymers are B-stage copolymers and networked copolymers. The term "B-stage" is defined as "an intermediate stage in a thermosetting resin reaction in which the plastic softens but does not fuse when heated, and swells but does not dissolve in contact with certain liquids", see McGraw-Hill Dictionary of Scientific & Technical Terms, 6E, Copyright 2003 by The McGraw-Hill Companies, Inc. The term "network" is defined as a covalently crosslinked 3-dimension polymer network in contrast to a "non-network polymer" or linear polymer which does not having a covalently crosslinked 3-dimension network.

The nature of the copolymers including its network form of the present invention address one or more of the shortcomings associated with known PIMs technology, e.g. increased membrane durability, rejection, fouling resistance, rigidity and dimensional stability leading to better maintenance of nanoporous structure under varied end uses conditions, better tolerance toward functional groups needed to enhance selectivity, improved processability and fabrication, higher glass transition temperature, higher thermal stability, higher thermooxidative stability, increased moisture resistance, increased corrosion resistance to acids and bases, and organic solvent resistance.

Membranes made using the subject copolymers may be formed by conventional techniques, e.g. casting, in-situ polymerization upon a porous support, dip coating and subsequent polymerization onto a porous support, etc. Such membranes are useful in separations based upon the relative rates of mass transfer of different species across a membrane. A driving force, typically a pressure or a concentration difference, is applied across the membrane so that selected species preferentially pass across the membrane. The membranes may be used for purification, separation or adsorption of a particular species (e.g. salts, organics, ionic species) in the liquid (e.g. aqueous, organic) or gas phase. In particular, the subject membranes exhibit excellent pH and solvent stability and as a consequence, are suitable for use in a wide range of applications including: gas separation, ion exchange, water softening, water purification, ultra high purity water production in applications such as electronics, metal separation including rare earths, catalysis, remediation of mining waste water, uranium processing, leach mining, and processing of liquids in dairy, sugar, fruit juice and pharmaceuticals and ethanol production in a continuous fermentation/membrane pervaporation system. In specific embodiments, the subject copolymers include hydrophilic functional groups, e.g. carboxylic acid, that provide improved selectivity in many applications.

The subject membrane is not particularly limited to a specific type, construction or application. For example, the subject polymers may be fabricated into to flat sheet (film), tubular and hollow fiber configurations that find utility in a variety of applications including gas separations, pervaporation, forward osmosis (FO), reverse osmosis (RO), nano filtration (NF), ultra filtration (UF), micro filtration (MF) and pressure retarded fluid separations. One preferred design is a thin film composite structure. See for example WO 2005/113121 and US2014/0251897. With a thin film composite design a "thin film" of the subject polymer is formed upon a support using well known techniques, e.g. dip coating, casting, etc., a solution of the subject polymer and conducting a phase separation (e.g. via quench, cooling, etc.) to form the desired porosity. The resulting membrane may be further subject to heating to facilitate crosslinking. By way of a more specific example, the composite membrane may include a bottom layer (back side) of a nonwoven backing web (e.g. PET scrim), a middle layer of a porous support having a typical thickness of about 25-125 μm and top layer (front side) comprising a thin film polymer layer having a thickness typically less than about 1 micron, e.g. from 0.01 micron to 1 micron but more commonly from about 0.01 to 0.1 μm. The porous support is typically a polymeric material having pore sizes which are of sufficient size to permit essentially unrestricted passage of permeate but not large enough so as to interfere with the bridging over of a thin film polymer layer formed thereon. For example, the pore size of the support preferably ranges from about 0.001 to 0.5 μm. Non-limiting examples of porous supports include those made of: polysulfone, polyether sulfone, polyimide, polyamide, polyetherimide, polyacrylonitrile, cross-linked polyacrylonitrile, poly(methyl methacrylate), polyethylene, polypropylene, and various halogenated polymers such as polyvinylidene fluoride. For most applications, the porous support provides strength but offers little resistance to fluid flow due to its relatively high porosity.

The invention includes copolymers having intrinsic microporosity and membranes made therefrom. In one embodiment, the invention includes a copolymer including a repeating unit represented by Formula I:

Formula I:

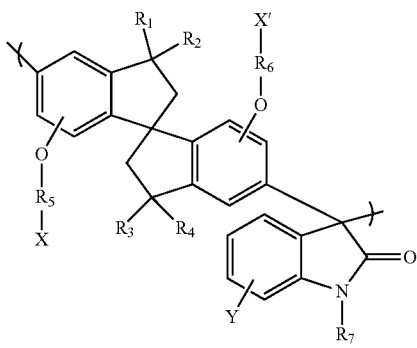

wherein:

Y is selected from: a carboxylic acid, sulfonic, phosphorous acid and phosphoric acid and their corresponding salt or ester, imino, amide; nitrile, hydrogen, hydroxyl and alkyl including from 1 to 6 carbon atoms, but is preferably hydrogen;

$R_1$, $R_2$, $R_3$, and $R_4$ are independently selected from: hydrogen, alkyl groups comprising from 1 to 6 carbon atoms, and $R_1$ and $R_2$ may collectively form a ketone group or a 9,9'-fluorene group, and $R_3$ and $R_4$ may collectively form a ketone group or a 9,9'-fluorene group, but is preferably selected from hydrogen and alkyl groups including from 1 to 6 carbon atoms;

$R_5$ and $R_6$ are independently selected from: a bond and an alkylene group including from 1 to 6 carbon atoms;

$R_7$ is selected from: hydrogen, alkyl, aryl, aralkyl and heteroaryl groups comprising from 1 to 8 carbon atoms which may be unsubstituted or substituted with carboxylic acid, sulfonic acid and phosphoric acid and their corresponding salt or ester, imino and amide; and X and X' are independently selected from: a carboxylic acid, sulfonic acid and phosphoric acid and their corresponding salt or ester, imino and amide; nitrile, hydrogen, alkyl having from 1 to 6 carbon atoms and alkoxy having from 1 to 6 carbon atoms.

In one preferred embodiment, X and X' are independently selected from a carboxylic acid, sulfonic acid and phosphoric acid and their corresponding salt or ester; or when $R_5$ and $R_6$ are a bond, X and X' are hydrogen. In another preferred embodiment, $R_1$, $R_2$, $R_3$, $R_4$ and $R_7$ are independently selected from hydrogen and alkyl groups comprising from 1 to 6 carbon atoms.

In another embodiment, at least one and in some instances both of the following definitions apply: i) X and X' are independently selected from a carboxylic acid, sulfonic acid and phosphoric acid and their corresponding salt or ester, imino and amide, and ii) $R_7$ is selected from alkyl, aryl, aralkyl and heteroaryl groups comprising from 1 to 8 carbon atoms which are substituted with carboxylic acid, sulfonic acid and phosphoric acid and their corresponding salt or ester, imino and amide.

The subject copolymers may include additional repeating units or branching, i.e. be formed via a copolymerization; however, the subject polymers preferably comprise at least 50 molar %, 75 molar % and more preferably at least 90 molar % of repeating units represented by Formula I (e.g. 50-100 molar %, 75-100 molar % and 90 to 100 molar % of the subject monomers).

The subject copolymer may be prepared using known starting materials and techniques. For example, isatin monomers can be generally prepared by the methods described by Charles M. Clay, Hagar M. Abdallah, Carly Jordan, Kyle Knisley, Daniel M. Ketcha, Archive for Organic Chemistry, volume 2012, issue 6, 317-325; Simon J. Garden, Jose C. Torres, Leonardo E. da Silva, Angelo C. Pinto, Synthetic Communications, 28(9), 1679-1689 (1998). Franciso Martinez, Herbert Naarmann, Synthetic Metals, 39, 195-203 (1990); Copolla, G. M., Journal of Heterocyclic Chemistry, 24, 1249-1251 (1987). The main isatin synthesis is the method of Sandmeyer which involves reaction of an aniline with chloral hydrate and hydroxylamine hydrochloride in aqueous sodium sulfate to form an isonitrosoacetanilide which is treated with sulfuric acid after its isolation, see: M. Alam, M. Younas, M. A. Zafar, Naeem, Pak. J. Sci. Ind. Res. 32, 246 (1989) (CA 112:7313u); S. J. Garden, J. C. Torres, A. A. Ferriera, R. B. Silva, A. C. Pinto, Tetrahedron Letters, 38, 1501 (1997); W. Prinz, A. Kayle, P. R. Levy, J. Chem. Res (S), 116 (1978). In a similar synthesis, isatins may also be prepared via cyclization of nitroacetanilides in acidic media to give isatin 3-oximes, see: T. Kearney, P. A. Harris, A. Jackson, J. A. Joule, Synthesis 769 (1992).

The Stolle procedure involves reaction of an aniline with oxalyl chloride to provide a chlorooxalylanilide intermediate which is cyclized to the isatin using a Lewis acid, see: W. M. Bryant, III; G. F. Huh; J. H. Jensen; M. E. Pierce; Synthetic Communications, 23, 1617 (1993); Y. Fukuda, Y. Itoh, K. Nakatani, S. Terashima, Tetrahedron, 50 2793 (1994). The Gassman procedure involves synthesis of a 3-methyl-2-oxindole and its oxidation to the isatin, see: P. G. Gassman, B. W. Cue, Jr; T. Y. Luh; J. Org. Chem., 42, 1344 (1977); P. G. Gassman, K. M. Halweg, J. Org. Chem., 44, 628 (1979); S. W. Wright, L. D. McClure, D. L. Hageman, Tetrahedron Letters, 37, 4631 (1996). The Martinet synthesis involves reaction of an aminoaromatic compound with an oxomalonate ester (or hydrate thereof) in acid media to form a 3-(3-hydroxy-2-oxindole)carboxylic acid followed by oxidative decarboxylation to the isatin, see: K. C. Rice, B. J. Boone, A. B. Rubin, T. J. Rauls, J. Med. Chem. 19, 887 (1976); A. Taylor, J. Chem Res., 347 (1980). Directed ortho-metalation of a N-pivaloyl or N-(t-butoxycarbonyl) aniline followed by reaction with diethyl oxalate, then deprotection and cyclization of the resultant a-ketoester intermediate provides the corresponding isatin, see: P. Hewawasam, N. Meanwell, Tetrahedron Letters, 35, 7303 (1994); C. Rivalle, E. Bisogni, Journal of Heterocylioc Chemistry, 34, 441 (1997); K. Smith, G. A. El-Hiti, hawes, A.C., Synlett, 945 (1999). A one-pot synthesis of isatins is accomplished via reaction of ethyl nitroacetate with a substituted benzene compound in polyphosphoric acid, see: N. A. Aksenov, A. V. Aksenov, I. V. Aksenova, Yu. I. Smushkevich, Chemistry of Heterocyclic Compounds, volume 49, issue 4, 645-647 (July, 2013). Numerous other useful syntheses of isatins are known.

Spirobisindane monomers may be prepared using the methods described by Chen, W-F.; Lin, H-Y.; Dai, S. A.; Organic Letters, 6, 14, 2341-2343 (2004); Faler, G. R.; Lynch, J. C.; U.S. Pat. No. 4,701,566 (Oct. 20, 1987); Ito, M.; Iimuro, S.; U.S. Pat. No. 5,339,783 (Mar. 21, 1995); Curtis, R. F.; Lewis, K. O.; J. Chem. Soc., 418-421 (1962); Baker, W.; J. Chem. Soc., 1678-1681 (1934); Fisher, C. H.; Furlong, R. W.; Grant, M.; Journal of the American Chemical Society 58, 820-822 (1936); Baker, W.; Besly, D. M.; J. Chem. Soc., 1421-1424 (1939); Baker, W.; Besly, D. M.; J. Chem. Soc., 347-353 (1938), Ma, X; Swaidan, Y. B.; Zhu, Y.; Litwiller, E.; Jouiad, I. P.; Han, Y.; Macromolecules, 45, 3841-3849 (2012); Li, S.; Jo, H. J.; Han, S. H.; Park, C. H.; Kim, S.; Budd, P. M.; Lee, Y. M.; Journal of Membrane Science, 434, 137-147 (2013). A representative reaction pathway is provided below for preparation of a spirobisindane bis(carboxylic acid). A representative reaction pathway for copolymerization of the subject copolymer is also provided below.

Reaction pathway I:

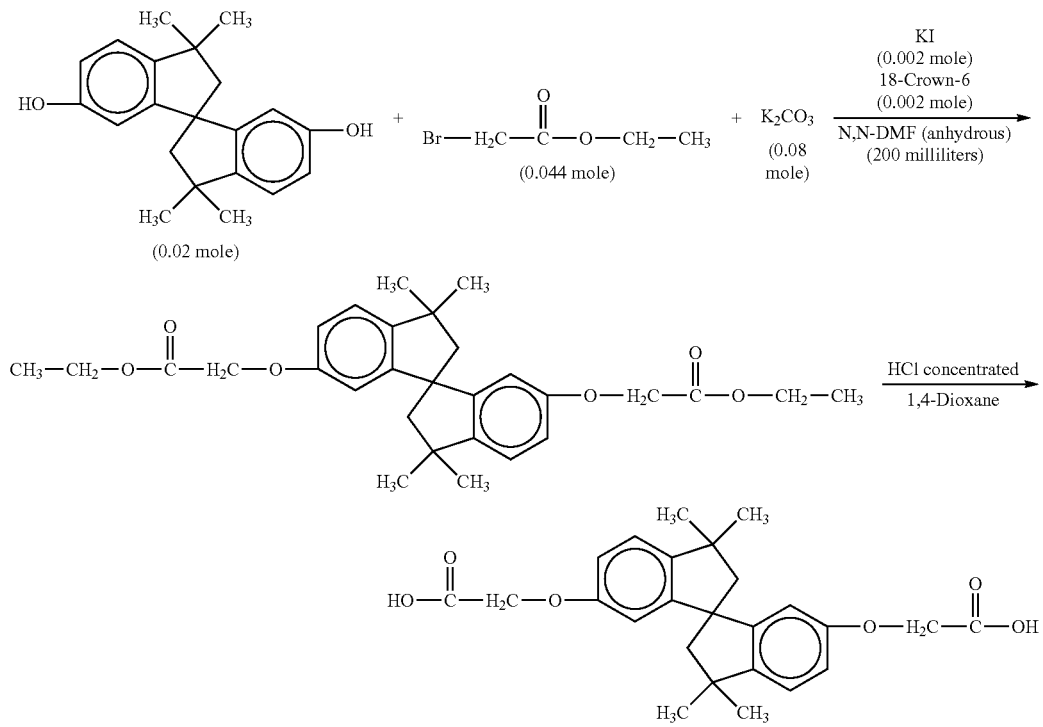

Reaction pathway II: (TFSA = trifluoromethanesulfonic acid)

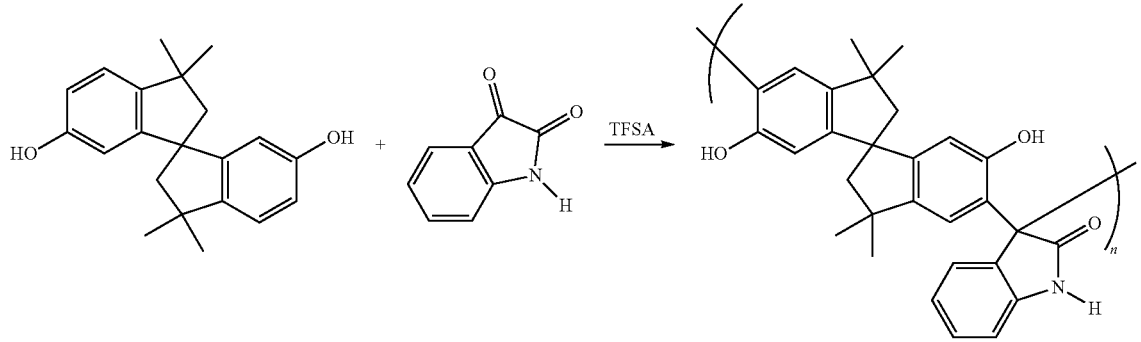

A number of variations are possible within the copolymer synthesis that are useful for modification of physical and mechanical properties. These variations include structural changes in the comonomers employed and changes in the stoichiometric ratio of comonomers employed. Examples of structural changes in the comonomers employed include addition of one or more substituents to the isatin aromatic ring and variations of comonomer, for example, from a carboxymethyl ether of a spirobisindanediol to another suitable carboxy functional aromatic comonomer such as spirobisindanedicarboxylic acid. Changes in the stoichiometric ratio of comonomers employed include: variations in equivalent ratio of comonomers used (can markedly change molecular weight and/or crosslink density), inclusion of additional comonomers, for example, (1) partial substitution (substitution of 1% wt. up to 95% wt., more preferably from 1% wt to 50% wt) of a functionalized isatin comonomer with isatin per se, and (2) use of a blend of carboxylic acid functional aromatic monomer, such as carboxymethyl ether of a spirobisindanediol with a non-carboxylic acid functional aromatic monomer, such as a spirobisindanediol (can adjust the carboxylic acid equivalency in the copolymer product). The functionalization of the finished thermoplastic polymers, e.g., to introduce N-carboxymethyl or N-alkyl sulfonic acid substituents, makes a good extension to the membrane separation application. The high hydrophilicity and surface charge are preferred for higher selectivity in gas separations, or water flux and solute rejection in liquid separations.

The many known methods can be adapted for crosslinking of the copolymers, e.g. amide formation can be adapted for crosslinking of the copolymers containing carboxylic acid groups. Formation of the amide typically requires activation of the carboxylic acid moiety with a coupling reagent. This activation converts the hydroxyl group of the carboxylic acid to a suitable leaving group, thus avoiding formation of a carboxylic acid salt with the amine reactant. The reaction of the activated intermediate with the amine is the coupling reaction and the activator used is the coupling reagent, see Han, S.-Y.; Kim, Y.-A. Tetrahedron 60, 2447 (2004). Depending upon the specific chemistry used, the reactive acylating agent may be formed in a separate reaction and then reacted with the amine or it may be formed in situ by adding the activating agent to the mixture of carboxylic acid and amine reactants. Additives, such as N-hydroxysuccinimide and 1-hydroxybenzotriazole, that enhance the reactivity of the coupling reagent, may also be used. A specific example is an additive that forms an active ester with the carboxylic acid, such as an O-acylisourea or a benzotriazole active ester. Coupling reagents may be prepared by reaction of a carboxylic acid ester to a hydrazide which is then urther reacted with nitrous acid or an alkyl nitrite to give the azide for reaction with the amine reactant. Diphenylphosphoryl azide can perform coupling in the presence of a base as a single high yield step, see Shioiri, T.; Ninomiya, K.; Yamada, S.; J. Am. Chem. Soc. 94, 6203 (1972). Reaction of a carboxylic acid phosphinothioester with an azide provides a iminophosphorane that rearranges to an amido phosphonium salt which hydrolyzes to the amide, see Nilsson, B. L.; Hondal, R. J.; Soellner, M. B.; Raines, R. T.; J. Am. Chem. Soc. 125, 5268 (2003). A mixed anhydride, for example, generated via reaction of pivaloyl chloride with the carboxylic acid group, is then reacted with the amine reactant to produce the amide. Ethyl chloroformate or isobutyl chloroformate are also used for synthesis of mixed carbonic anhydrides. A separate reaction of the carboxylic acid with the chloroformate is typically followed by reaction of the resultant mixed carbonic anhydride with the amine compound. Mixed ethyl carbonic anhydrides can be synthesized via reaction of a carboxylic acid with 1-ethoxycarbonyl-2-ethoxy-1,2-dihydroquinoline in the presence of the amino component as a single step direct coupling, see Belleau, B.; Malek, G.; J. Am. Chem. Soc. 90 (1968).

Carboxylic acids may be crosslinked by a primary amine compound in the presence of a carbodiimide compound to prepare an oligomer or polymer simultaneously containing nanoporosity. In the reaction, one or more carboxylic acid groups are reacted with one or more primary amine containing compounds (monoamine, diamine, and/or polyamines may be used) and one or more carbodiimide crosslinking agents. For crosslinking in aqueous media, a water-soluble carbodiimide is employed, such as 1-ethyl-3-(-3-dimethylaminopropyl) carbodiimide hydrochloride. For crosslinking in non-aqueous media, an organic solvent soluble carbodiimide is employed, such as N',N'-dicyclohexyl carbodiimide. In the crosslinking chemistry, the carbodiimide reacts with carboxylic acid group to form an active O-acylisourea intermediate that is easily displaced by nucleophilic attack from a primary amino group in the reaction mixture. Reaction with the primary amine results in an amide bond formed with the original carboxyl group, with the carbodiimide by-product released as an urea derivative. 1-Ethyl-3-(-3-dimethylamino propyl) carbodiimide hydrochloride crosslinking is most efficient in acidic (pH 4.5) conditions and must be performed in buffers devoid of extraneous carboxyls and amines. 4-Morpholinoethanesulfonic acid buffer is a suitable carbodiimide reaction buffer. Phosphate buffers and neutral pH (up to 7.2) conditions are compatible with the reaction chemistry, but with lower efficiency.

B-staging or prepolymerization of copolymerizable mixtures wherein at least one comonomer (the isatin monomer and/or the spirobisindane monomer) contains a thermosettable moiety can be accomplished by using lower temperatures and/or shorter curing times and /or reduced catalyst concentration. Curing of the thus formed B-staged (prepolymerized) copolymers can then be accomplished at a later time or immediately following B-staging (prepolymerization) by increasing the temperature and/or curing time.

EXAMPLES

Example 1

In a 100 ml round glass three-necked flask, a mixture of isatin (0.255 g, 1.73 mmol), 3,3,3',3'-tetramethyl-1,1'-spirobisindane-6,6'-diol (0.416 g, 1.35 mmol), dichloromethane (2.0 mL), trifluoroacetic acid (TFA) (2.5 mL), and trifluoromethanesulfonic acid (TFSA) (0.4 mL) was stirred at room temperature for 105 min and precipitated into methanol/water (v/v,1:1) mixture. The white fiber like solid formed was filtered off and washed with deionized water to afford 0.5 g product (yield: 84%). $^1$H NMR (DMSO-$d_6$, ppm): 10.62-11.18 (br, 1H), 9.42-10.22 (br, 1H), 8.82-9.36 (br, 1H), 5.84-7.41 (br, 8H), 1.81-2.46 (br, 4H), 0.76-1.52 (br, 12H). GPC: Mn=60779, Mw=148020, PDI=2.43; TGA: Td=334.6° C. The general reaction is illustrated by Reaction Pathway II, shown above. The resulting copolymer was tested for solubility (Table 1), thermal stability and porosity (Table 2), the results of which are provided below. The solubility of the inventive example 1 is improved over polymers commonly used in making membranes. As an additional comparison, solubility data is also provided for an isatin copolymer ("PI-1") as described in U.S. Pat. No. 7,771,857.

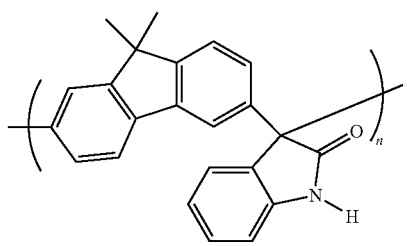

PI-1

TABLE 1

Polymer solubility (o: soluble, x: insoluble, Δ: swell).

| Polymer | DMF | DMF/IPA (2/8-4/6) w/w | DMF/DEG (2/8-4/6) w/w | THF | MEK |
|---|---|---|---|---|---|
| PI-1 (Comparative Ex. 1) | o | x | x | x | x |
| Polyacrylonitrile (Comparative Ex. 2) | o | x | x | x | x |
| Polysulfone (Comparative Ex. 3) | o | x | x | o | Δ |
| Example 1 | o | o | o | o | o |

IPA = isopropanol;
DEG = diethylene glycol;
EGME = ethylene glycol monomethyl ether
DMF = Dimethylformamide;
THF = Tetrahydrofuran;
MEK = Methylethyl ketone

TABLE 2

Thermal and porosity properties

| Polymers | $T_d$/° C. | Surface area (m²/g) single point | BET |
|---|---|---|---|
| Example 1 | 334.6 | 293.66 | 296.34 |

What is claimed is:

1. A copolymer comprising a repeating unit represented by:

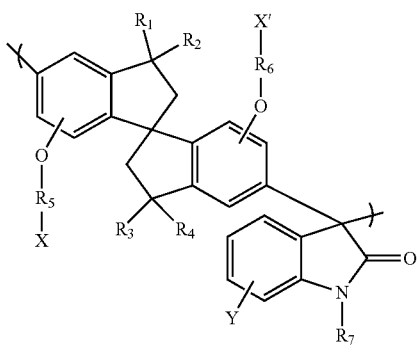

wherein:
Y is selected from: a carboxylic acid, sulfonic, phosphorous acid and phosphoric acid and their corresponding salt or ester, imino, amide; nitrile, hydrogen, hydroxyl and alkyl comprising from 1 to 6 carbon atoms; and $R_1$, $R_2$, $R_3$, and $R_4$ are independently selected from: hydrogen, alkyl groups comprising from 1 to 6 carbon atoms, and $R_1$ and $R_2$ may collectively form a ketone group or a 9,9'-fluorene group, and $R_3$ and $R_4$ may collectively form a ketone group or a 9,9'-fluorene group;

$R_5$ and $R_6$ are independently selected from: a bond and an alkylene group comprising from 1 to 6 carbon atoms;

$R_7$ is selected from: hydrogen, alkyl, aryl, aralkyl and heteroaryl groups comprising from 1 to 8 carbon atoms which may be unsubstituted or substituted with carboxylic acid, sulfonic acid and phosphoric acid and their corresponding salt or ester, imino and amide; and X and X' are independently selected from: a carboxylic acid, sulfonic acid and phosphoric acid and their corresponding salt or ester, imino and amide; nitrile, hydrogen, alkyl having from 1 to 6 carbon atoms and alkoxy having from 1 to 6 carbon atoms.

2. The copolymer of claim 1 wherein Y is hydrogen.

3. The copolymer of claim 1 wherein $R_1$, $R_2$, $R_3$, $R_4$ and $R_7$ are independently selected from hydrogen and alkyl groups comprising from 1 to 6 carbon atoms; and X and X' are independently selected from a carboxylic acid, sulfonic acid and phosphoric acid and their corresponding salt or ester, imino and amide; or when $R_5$ and $R_6$ are a bond, X and X' are hydrogen.

4. The copolymer of claim 1 wherein at least one of:
i) X and X' are independently selected from a carboxylic acid, sulfonic acid and phosphoric acid and their corresponding salt or ester, imino and amide, and
ii) $R_7$ is selected from alkyl, aryl, aralkyl and heteroaryl groups comprising from 1 to 8 carbon atoms which are substituted with carboxylic acid, sulfonic acid and phosphoric acid and their corresponding salt or ester, imino and amide.

5. The copolymer of claim 1 characterized by being a network polymer.

6. The copolymer of claim 1 characterized by having an average pore size of from 0.2 to 20 nm as determined by ASTM F316-03 (2011).

7. The copolymer of claim 1 characterized by having an apparent surface area of greater than 100 m$^2$/g as measured by the Brunauer-Emmett-Teller (BET) method.

8. A membrane comprising the copolymer of claim 1.

* * * * *